(12) United States Patent
Kuchta et al.

(10) Patent No.: US 7,399,874 B2
(45) Date of Patent: Jul. 15, 2008

(54) CATALYST COMPOUND CONTAINING DIVALENT TRIDENTATE LIGAND

(75) Inventors: Matthew C. Kuchta, San Rafael, CA (US); David H. McConville, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 122 days.

(21) Appl. No.: 11/221,990

(22) Filed: Sep. 8, 2005

(65) Prior Publication Data

US 2006/0094842 A1 May 4, 2006

Related U.S. Application Data

(60) Provisional application No. 60/623,673, filed on Oct. 29, 2004.

(51) Int. Cl.
*C07F 15/04* (2006.01)
*B01J 31/18* (2006.01)

(52) U.S. Cl. .................. 556/137; 502/155; 502/167; 526/161; 526/171; 526/172

(58) Field of Classification Search .............. 502/155, 502/167; 526/161, 171, 172; 556/137
See application file for complete search history.

(56) References Cited

U.S. PATENT DOCUMENTS

| | | | | |
|---|---|---|---|---|
| 5,318,935 | A | 6/1994 | Canich et al. | 502/117 |
| 5,506,184 | A | 4/1996 | Kissin et al. | 502/115 |
| 5,576,460 | A | 11/1996 | Buchwald et al. | 564/386 |
| 5,880,323 | A | 3/1999 | Brookhart et al. | 585/527 |
| 5,889,128 | A | 3/1999 | Schrock et al. | 526/107 |
| 6,103,657 | A | 8/2000 | Murray | 502/155 |
| 6,255,414 | B1 | 7/2001 | Ittel et al. | 526/115 |
| 2004/0110983 | A1* | 6/2004 | Odom | 564/225 |

FOREIGN PATENT DOCUMENTS

| | | |
|---|---|---|
| DE | 41 20 344 | 1/1992 |
| EP | 0 893 454 | 1/1999 |
| EP | 1 008 595 | 6/2000 |
| EP | 1 170 308 | 1/2002 |
| EP | 0 834 514 | 10/2003 |
| JP | 2000302810 | 10/2000 |
| JP | 2001181333 | 7/2001 |
| JP | 2001261638 | 9/2001 |
| JP | 2001261639 | 9/2001 |
| JP | 2002332312 | 11/2002 |
| WO | 96/23101 | 8/1996 |
| WO | 96/33202 | 10/1996 |
| WO | 97/02298 | 1/1997 |
| WO | 00/69922 | 11/2000 |
| WO | 01/30860 | 5/2001 |
| WO | 01/30861 | 5/2001 |
| WO | 02/090366 | 11/2002 |
| WO | 2004/053458 | 6/2004 |

OTHER PUBLICATIONS

Abstract Only—Kempe et al., "Aminopyridinato Ligands-New Directions and Limitations," 80th Canadian Society for—Chemistry Meeting, Windsor, Ontario, Canada, Jun. 1-4, 1997.
Clark et al., "Titanium(IV) complexes incorporating the aminodiamide ligand [(SiMe$_3$)N {CH$_2$CH$_2$N(SiMe$_3$)}$^2$ (L) ; the X-ray crystal structures of [TiMe$_2$(L)] and [TiCl{CH(SiMe$_3$)$_2$}(L)]",Journal of Organometallic Chemistry, 501 (1995) pp. 333-340.
Horton et al., "Cationic Alkylzirconium Complexes Based on a Tridentate Diamide Ligand: New Alkene Polymerization Catalysts", Organometallics 1996, 15, pp. 2672-2674.
Guerin et al., "Conformationally Rigid Diamide Complexes of Zirconium: Electron Deficient Analogues of Cp$_2$Zr", Organometallics 1996, 15, pp. 5586-5590.
Guerin et al., "Conformationally Rigid Diamide Complexes: Synthesis and Structure of Titanium(IV) Alkyl Derivatives", Organometallics 1996, 15, pp. 5085-5089.
Bei et al., "Synthesis, Structures, Bonding, and Ethylene Reactivity of Group 4 Metal Alkyl Complexes Incorporating 8-Quinolinolato Ligands", Organometallics 1997, 16, pp. 3282-3302.

(Continued)

*Primary Examiner*—Robert D. Harlan
(74) *Attorney, Agent, or Firm*—Catherine L. Bell

(57) ABSTRACT

This invention relates to a catalyst compound represented by the formula:

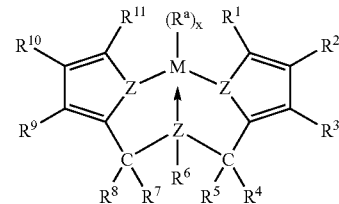

wherein:
M is a Group 3 to 12 transition metal;
each $R^a$ is, independently, a hydrogen, a hydrocarbyl group, a substituted hydrocarbyl group or halogen;
each of $R^1$, $R^2$, $R^3$, $R^4$, $R^5$, $R^7$, $R^8$, $R^9$, $R^{10}$, and $R^{11}$ is, independently a hydrogen, a hydrocarbyl group, a substituted hydrocarbyl group or halogen;
$R^6$ is hydrogen, a hydrocarbyl group, or a substituted hydrocarbyl group;
x is 0, 1, 2, 3 or 4; and
each Z is, independently, a group 15 atom.

This invention also relates to catalyst systems comprising the above catalyst compound and a activator and the use of such catalyst systems to polymerize monomers, including olefin monomers.

37 Claims, No Drawings

OTHER PUBLICATIONS

Thornberry et al., "Structural and Electronic Effects of Pentafluorophenyl Substituents on Cyclopentadienyl Complexes of Fe, Co, Mn and Re[1]", Organometallics 2000, 19, pp. 5352-5369.

Schrodi et al., "Cationic Zirconium Complexes that Contain Mesityl-Substituted Diamido/Donor Ligands. Decomposition via CH Activation and Its Influence on 1-Hexene Polymerization", Organometallics 2001, 20, pp. 3560-3573.

Cao et al., "Hydroamination of Alkynes Catalyzed by a Titanium Pyrrolyl Complex", Organometallics 2001, 20, pp. 5011-5013.

Schrock et al., "CH Bond Activation in Cations of the Type {[(2,4,6-Me$_3$C$_6$H$_2$NCH$_2$CH$_2$)$_2$NMe]ZrR}+ and a Simple Solution that Yields a Catalyst for the Living Polymerization of 1-Hexene", Organometallics 2001, 20, pp. 1056-1058.

Tshuva et al., "Zirconium Complexes of Amine-Bis(phenolate) Ligands as Catalysts for 1-Hexene Polymerization: Peripheral Structural Parameters Strongly Affect Reactivity", Organometallics 2001, 20, pp. 3017-3028.

Huang, et al., "Zirconium Complexes Containing Bidentate Pyrrole Ligands: Synthesis, Structural Characterization, and Ethylene Polymerization", Organometallics 2001, 20, pp. 5788-5791.

Tanski et al., "Synthesis and Structures of Zirconium-Pyrrolyl Complexes: Computational Analysis of the Factors that Influence the Coordination Modes of Pyrrolyl Ligands", Organometallics 2002, 21, pp. 587-589.

Cao et al., "A Titanium-Catalyzed Three-Component Coupling to Generate α,β-Unsaturated β-Iminoamines", J. Am. Chem. Society, 2003, 125, pp. 2880-2881.

Li et al., "Titanium Hydrazido and Imido Complexes: Synthesis, Structure, Reactivity, and Relevance to Alkyne Hydroamination", J. Am. Chem. Soc., 2004, 126, pp. 1794-1803.

Cao et al., "Intermolecular Alkyne Hydroaminations Involving 1,1-Disubstituted Hydrazines", Organic Letters, 2002, vol. 4, No. 17, pp. 2853-2856.

Ramanathan et al., "Pyrrole Syntheses Based on Titanium-Catalyzed Hydroamination of Diynes", Organic Letters, 2004, vol. 6, No. 17, pp. 2957-2960.

Scollard et al., "Living Polymerization of α-Olefins by Chelating Diamide Complexes of Titanium", J. Am. Chem. Soc. 1996, 118, pp. 10008-10009.

Baumann et al., "Synthesis of Titanium and Zirconium Complexes That Contain the Tridentate Diamido Ligand, [((t-Bu-d$^6$)N-o-C$_6$H$_4$)$_2$O]$^{2-}$ ([NON]$^{2-}$) and the Living Polymerization of 1-Hexene by Activated [NON]ZrMe$_2$", J. Am. Chem. Soc. 1997, 119, pp. 3830-3831.

Mehrkhodavandi et al., "Cationic Hafnium Alkyl Complexes that Are Stable toward β-Hydride Elimination below 10° C and Active as Initiators for the Living Polymerization of 1-Hexene", J. Am. Chem. Soc, 2001, 123, pp. 10746-10747.

Fuhrmann et al., "Octahedral Group 4 Metal Complexes that Contain Amine, Amido, and Aminopyridinato Ligands: Synthesis, Structure, and Application in α-Olefin Oligo- and Polymerization", Inorg. Chem. 1996, 35, pp. 6742-6745.

Tshuva et al., "Coordination Chemistry of Amine Bis(phenolate) Titanium Complexes: Tuning Complex Type and Structure by Ligand Modification", Inorg. Chem. 2001, 40, pp. 4263-4270.

Harris et al., "Titanium η$^1$-Pyrrolyl Complexes: Electronic and Structural Characteristics Imposed by the N,N-Di(pyrrolyl-α-methyl)-N-methylamine (dpma) Ligand", Inorg. Chem. 2001, 40, pp. 1987-1988.

Ciszewski et al., Investigation of Transition Metal-Imido Bonding in M(NBu$_1$)$_2$(dpma), Inorg. Chem. 2004, 43, pp. 3605-3617.

Li et al., Group-4 η$^1$-Pyrrolyl Complexes Incorporating N,N-Di(pyrrolyl-α-methyl)-N-methylamine, Inorg. Chem. 2002, 41, pp. 6298-6306.

Shi et al., "Synthesis and Group 4 Complexes of Tris(pyrrolyl-α-methyl)amine", Inorg. Chem. 2004, 43, pp. 275-281.

Zhuang et al., "Synthesis of optically active amino sugar derivatives using catalytic enantioselective hetero-Diels-Alder reactions", Chem. Commun., 2000, pp. 459-460.

Shi et al., "Titanium dipyrrolylmethane derivatives: rapid intermolecular alkyne hydroamination", Chem. Commun. 2003, pp. 586-587.

Sernetz et al., "Copolymerization of Ethene with Styrene Using Methylaluminoxane-Activated Bis(phenolate) Complexes", Macromolecules, 1997, 30, pp. 1562-1569.

Huang et al., Metal Imido Complexes (M=Ti, W) Containing 2-(Dimethylaminomethyl)pyrrole: Synthesis and the Crystal Structures of Bu$^t$N=TiClPy$_2$[2-Me$_2$NCH$_2$(C$_4$H$_3$N)] and PhN=WCl$_3$[2-Me$_2$NCH$_2$(C$_4$H$_3$N)], Journal of the Chinese Chemical Society, 2000, 47, pp. 895-900.

Friedrich et al., "A New Class of Five-co-ordinate Titanium Complexes containing a Polyfunctional Amido Ligand. Crystal Structure of [TiBr$_2${CH(2-C$_5$H$_4$N)(CH$_2$NSiMe$_3$)$_2$}]", J. Chem. Soc. Dalton Trans. 1993, pp. 2861-2862.

Cloke et al., "Zirconium Complexes incorporating the New Tridentate Diamide Ligand [(Me$_3$Si)N{CH$_2$CH$_2$N(SiMe$_3$)}$_2$]$^{2-}$ (L); the Crystal Structures of [Zr(BH$_4$)$_2$L] and [ZrCl{CH(SiMe$_3$)$_2$}L]", J. Chem. Soc. Dalton Trans. 1995, pp. 25-30.

Male et al., "Synthesis and structure of zirconium(IV) alkyl complexes with bi-, tri, tetra- and penta-dentate amido ligands", J. Chem. Soc. Dalton Trans. 1997, pp. 2487-2494.

Matsuo et al., Synthesis and Characterization of Bis(iminopyrrolyl)zirconium Complexes, Chemistry Letters, 2000, pp. 1114-1115.

Choukroun et al., "Reactivity of the Titanium-Nitrogen Bond in the Mixed Trisalkoxy Dialkylamido Derivative Ti(OR)$_3$(NEt$_2$): Substitution and Insertion Reactions", Inorg. Met. Org. Chem., 8(2), (1978) pp. 137-147.

Dias et al., "Synthesis, Characterization and Theoretical Evaluation of [Ti(NC$_4$Me$_4$)(NMe$_2$)$_3$]- A Complex with N-Bonded 2,3,4,5-Tetra-Methylpyrrolyl Ligand", Collect. Czech. Chem. Commun (vol. 63) (1998), pp. 182-186.

Burger et al., "Zeitschrift fur anorganische und allgemeine Chemie", Z. anorg. allg. Chemie, Bd, 394, pp. 209-216.

Zeitschrift Fur Naturforschung, Jul. 1970, Band 25 b, Heft 7, pp. 1358-1363.

Yoshida et al., "Post-Metallocenes: new Bis(pyrrolyl-2-aldiminato) Titanium Complexes for Ethylene Polymerization", Chemistry Letters, 2000, pp. 1270-1271.

Bradley et al., "Metallo-organic Compounds Containing Metal-Nitrogen Bonds, Part V.[1] Dialkylamidopyrrolyl- and Dialkylamido-2,5-dimethyl-pyrrolyl-titanium Compounds", Inorg. Phys. Theor., pp. 1967-1969.

Burger et al., "Darstellung und Eigenschaften von Ti-substituierten N-Heterocyclen[1]", Z. anorg. allg. Chem. 407, (1974) pp. 201-210.

Kempe et al., "Aminopyridinato Ligands—New Directions and Limitations", 80th Canadian Society for -Chemistry Meeting, Windsor, Ontario, Canada, Jun. 1-4, 1997.

Huang et al, "Synthesis and Structure Characterization of 2-(Dimethylaminomethyl)pyrrolate and 2,5-Bis(dimethylaminomethyl)pyrrolate Zirconium Complexes", Journal of the Chinese Chemical Society, 2000, 47, pp. 1191-1195.

Schrock et al., "Preparation and Activation of Complexes of the Type [((mesityl)NCH$_2$CH$_2$)$_2$NX]ZrMe$_2$ (X = H, Me) with [Ph$_3$C][B(C$_6$F$_5$)$_4$] or [PhNMe$_2$H][B(C$_6$F$_5$)$_4$]", Organometallics, 2000, 19, pp. 5325-5341.

* cited by examiner

CATALYST COMPOUND CONTAINING DIVALENT TRIDENTATE LIGAND

CROSS REFERENCE TO RELATED APPLICATION

This application claims priority to U.S. Provisional Patent Application No. 60/623,673, filed Oct. 29, 2004.

FIELD OF THE INVENTION

The invention relates to a metal compound having a divalent tridentate ligand useful as an olefin polymerization catalyst and to processes for polymerizing olefins using the metal compound.

BACKGROUND OF THE INVENTION

A variety of metallocenes and other single site catalysts have been developed to prepare olefin polymers. Metallocenes are organometallic complexes containing one or more π-bonded moieties (i.e., cyclopentadienyl groups) in association with a metal atom. Catalyst compositions containing metallocenes and other single site catalysts are highly useful in the preparation of polyolefins, producing relatively homogeneous copolymers at excellent polymerization rates while allowing one to tailor the final properties of the polymer as desired.

Work relating to certain nitrogen-containing single site catalyst precursors has been published. WO 96/23101 and U.S. Pat. No. 5,880,323 relate to di(imine) metal complexes that are transition metal complexes of certain bidentate ligands, wherein the transition metal is selected from the group consisting of Ti, Zr, Sc, V, Cr, a rare earth metal, Fe, Co, Ni, and Pd.

Similarly, WO 97/02298 relates to a process for the polymerization of an olefin, comprising contacting a polymerizable monomer consisting essentially of ethylene, a norbornene or a styrene, with a catalyst system comprising the product of mixing in solution a zerovalent tricoordinate or tetracoordinate nickel (II) compound which has at least one labile ligand, and all ligands are neutral, an acid of the formula HX, and another compound. Likewise, WO 96/33202 relates to a transition metal catalyst containing a pyridine or quinoline moiety. Fuhrmann et al., Inorg. Chem., 35:6742-6745 (1996) discloses certain Group 4 metal complexes containing amine, amido, and aminopyridinato ligands. U.S. Pat. No. 6,103,657 describes a family of heteroatom-containing catalyst precursors useful for the polymerization of olefins. U.S. Pat. No. 6,255,414 describes the polymerization of olefins using catalysts, which are bridged transition metal complexes of bis(carboximidamidatonates).

WO 01/30861, and Guerin et al, "Confirmationally Rigid Diamide Complexes of Zirconium: Electron Deficient Analogues of Cp2Zr", Organometallics, Vol 15, No. 26, pp. 5586-5590, 1996, describe bidentate and tridentate ligated Group 3 to 14 metal compounds.

Anionic, multidentate heteroatom ligands are discussed in the following articles:

(1) Kempe et al., "Aminopyridinato Ligands—New Directions and Limitations", 80$^{th}$ Canadian Society for—Chemistry Meeting, Windsor, Ontario, Canada, Jun. 1-4, 1997;
(2) Jordan et al, of polyolefin catalysts based on hydroxyquinolines (Bei, X.; Swenson, D. C.; Jordan, R. F., *Organometallics* 1997, 16, 3282);
(3) Horton, et. al., "Cationic Alkylzirconium Complexes Based on a Tridentate Diamide Ligand: New Alkene Polymerization Catalysts", Organometallics, 1996, 15, 2672-2674 relates to tridentate zirconium complexes;
(4) Baumann, et al., "Synthesis of Titanium and Zirconium Complexes that Contain the Tridentate Diamido Ligand [((t-Bu-d$_6$)N—O—C$_6$H$_4$)$_2$O]$^{2-}$ {[NON]$^{2-}$) and the Living Polymerization of 1-Hexene by Activated [NON]ZrMe2", Journal of the American Chemical Society, Vol. 119, pp. 3830-3831;
(5) Cloke et al., "Zirconium Complexes incorporating the New Tridentate Diamide Ligand [(Me$_3$ Si)N{CH$_2$CH$_2$N (SiMe$_3$)}$_2$]$^{2-}$(L); the Crystal Structure of [Zr(BH$_4$)$_2$L] and [ZrCl{CH(SiMe$_3$)$_2$}L]", J, Chem. Soc. Dalton Trans, pp. 25-30, 1995;
(6) Clark et al, "Titanium (IV) complexes incorporating the aminodiamide ligand [(SiMe$_3$)N {CH$_2$CH$_2$N (SiMe$_3$)}$_2$]$^{2-}${L); the X-ray crystal structure of [TiMe$_2$(L)] and [TiCl{CH(SiMe$_3$)$_2$}(L)]", Journal of Organometallic Chemistry, Vol 50, pp. 333-340, 1995;
(7) Scollard et al., "Living Polymerization of alpha-olefins by Chelating Diamide Complexes of Titanium", J. Am. Chem. Soc., Vol 118, No. 41, pp. 10008-10009, 1996; and
(8) Guerin et al., "Conformationally Rigid Diamide Complexes: Synthesis and Structure of Titanium (IV) Alkyl Derivatives", Organometallics, Vol 15, No. 24, pp. 5085-5089, 1996.

Furthermore, U.S. Pat. No. 5,576,460 describes a preparation of arylamine ligands and U.S. Pat. No. 5,889,128 discloses a process for the living polymerization of olefins using initiators having a metal atom and a tridentate-ligand containing two group 15 atoms and a group 16 atom or three group 15 atoms. EP 893 454 A1 also describes titanium transition metal amide compounds. In addition, U.S. Pat. No. 5,318,935 discusses amido transition metal compounds and catalyst systems especially for the producing isotactic polypropylene. Polymerization catalysts containing bidentate and tridentate ligands are further discussed in U.S. Pat. No. 5,506,184.

Group 4 pyrrolide compounds are described in Inorg. Chem. 2001, 40, 1987; Organometallics 2001, 20, 5788; and Organometallics 2002, 21, 587. *Bradley and Chivers*, Inorg. Phys. Theor., J. Chem. Soc. (A) 1969 pg 1967-1969; Journal of the Chinese Chemical Society, 2000, 47, 1191-1195; Chemistry Letters 2000 Chemical Society of Japan, pg 1114-1115; Chemistry Letters 2000 Chemical Society of Japan, pg 1270-1271; Zeitschrift Fur Naturforschung, July 1970 Band 25b, Heft 7, pg 1358-1363; Z. Anorg. Allg. Chem. 407, 201-210, 1974; Zeitschrift fur Anorganische und Allgemeine Chemie, band 394, Heft 3, December 1972, pg 209-216; Collect. Czech. Chem. Commun. (vol. 63) 1988, pg 182-186; Journal of the Chinese Chemical Society, 2000, 47, 895-900; Synth. React. Inorg. Met.-Org. Chem., 8(2), 137-147 (1978); JP 2001-261638A1 (published Sep. 26, 2001); JP 2001 261639A (published Sep. 26, 2001); JP 2001 181333A (published Jul. 3, 2001); JP 2000 302810A (published Oct. 31 2000); and JP 2002 332312A (published Nov. 22, 2002).

Dianionic tridentate-ligand group 4 compounds are described in Inorg. Chem. 2001, 40, 4263; Organometallics 2001, 20, 3017; Macromolecules 1997, 30, 1562; Organometallics, 2001, 20, 1056; JACS 2001, 123, 10746; Organometallics 2000, 19, 5352; Organometallics, 2001, 20, 3560; Dalton Trans. 1993, 2861; WO 00/69922A1; and WO 01/30860A1; EP1170308A2; WO02/090366; Chem Commun. 2000, 459; EP0834514A2; Organic Letters 2002, 4, 2853; J. Chem. Soc. Dalton Trans. 1997, 2487; JACS 2003, 125, 2880; EP1008595A2; and DE4120344.

SUMMARY OF THE INVENTION

The invention relates to a compound represented by the formula (I):

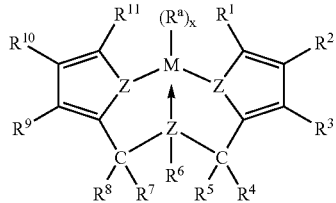

wherein:
M is a Group 3 to 12 transition metal;
each $R^a$ is, independently, a hydrogen, a hydrocarbyl group, a substituted hydrocarbyl group or halogen;
each of $R^1$, $R^2$, $R^3$, $R^4$, $R^5$, $R^7$, $R^8$, $R^9$, $R^{10}$, and $R^{11}$ is, independently a hydrogen, a hydrocarbyl group, a substituted hydrocarbyl group or halogen;
$R^6$ is hydrogen, a hydrocarbyl group, or a substituted hydrocarbyl group;
x is 0, 1, 2, 3 or 4;
each Z is, independently, a group 15 atom.

It is understood that the above formula encompass all possible stereoisomers, resonance structures and tautomers connoted by the structure of the formula.

This invention also relates to combinations of the above catalyst compound with activators, and their use to polymerize olefins.

Definitions

As used herein, the numbering scheme for the Periodic Table Groups is the new notation as set out in Chemical and Engineering News, 63(5), 27 (1985).

For the purposes of this invention and the claims thereto when a polymer is referred to as comprising an olefin, the olefin present in the polymer is the polymerized form of the olefin. Likewise when catalyst components are described as comprising neutral stable forms of the components, it is well understood by one of ordinary skill in the art, that it is the catalytically active form (typically the ionic form) of the component that reacts with the monomers to produce polymers. In addition, a reactor is any container(s) in which a chemical reaction occurs.

In the context of this document, "homopolymerization" would produce a polymer made from one monomer. For example, homopolymerization of propylene would produce homopolypropylene. Homopolymerization of ethylene would produce homopolyethylene. Likewise, "copolymerization" would produce polymers with more than one monomer type.

As used herein, Me is methyl, Et is ethyl, t-Bu and tBu are tertiary butyl, s-Bu and sBu is sec-butyl, i-Bu and iBu are isobutyl, iPr and iPr are isopropyl, Cy is cyclohexyl, and Ph is phenyl.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be C1-C100 radicals, that may be linear, branched, or cyclic, and when cyclic, aromatic or non-aromatic, and include substituted hydrocarbyl radicals, halocarbyl radicals, and substituted halocarbyl radicals, silylcarbyl radicals, and germylcarbyl radicals as these terms are defined below. When referring to a hydrogen substitutent, the terms "hydrogen," "hydride," and "hydrogen radical" are used interchangeably.

Substituted hydrocarbyl radicals are radicals in which at least one hydrogen atom has been substituted with at least one functional group such as, but not limited to, $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as, but not limited to, —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst precursor, catalyst compound, and transition metal compound or complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

DETAILED DESCRIPTION

In a preferred embodiment, this invention relates to a transition metal compound represented by the formula (II):

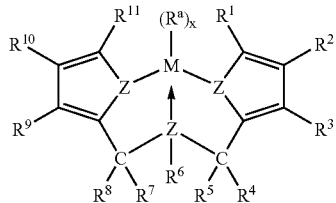

wherein
M is a Group 3 to 12 transition metal, preferably a Group 4 to 11 metal, preferably a Group 4 to 9 metal, preferably a Group 4 to 6 metal, preferably a Group 4 or 5 metal, preferably Ti, Zr, Hf, V, Cr, Fe, Co or Ni, more preferably Ti, Zr, Hf, or V, preferably Ti, Zr, or Hf;

each $R^a$ is, independently, a hydrogen, a hydrocarbyl group, a substituted hydrocarbyl group or halogen, preferably each $R^a$ is, independently, selected from the group consisting of chloride, bromide, fluoride, iodide, hydride, and C1 to C30 hydrocarbyls, preferably methyl, ethyl, propyl, butyl, pentyl, hexyl, phenyl, benzyl, and all isomers thereof;

each of $R^1$, $R^2$, $R^3$, $R^4$, $R^5$, $R^7$, $R^8$, $R^9$, $R^{10}$, and $R^{11}$ is, independently a hydrogen, a hydrocarbyl group, a substituted hydrocarbyl group or halogen, preferably each of $R^1$, $R^2$, $R^3$, $R^4$, $R^5$, $R^7$, $R^8$, $R^9$, $R^{10}$, and $R^{11}$ is, independently, selected from hydrogen or from the group consisting of C1 to C30 hydrocarbyls, preferably methyl, ethyl, propyl, butyl, pentyl, hexyl, heptyl, octyl, nonyl, decyl, undecyl, dodecyl, phenyl, C7 to C30 substituted phenyls, and all isomers thereof; more preferably each is, independently, selected from hydrogen or from the group consisting of methyl, ethyl, n-propyl, iso-propyl, n-butyl, s-butyl, i-butyl, t-butyl, n-hexyl, cyclohexyl, phenyl, tolyl, mesityl, and naphthyl;

$R^6$ is hydrogen, a hydrocarbyl group, a substituted hydrocarbyl group, preferably $R^6$ is selected from hydrogen or from the group consisting of C1 to C30 hydrocarbyls, preferably methyl, ethyl, propyl, butyl, pentyl, hexyl, heptyl, octyl, nonyl, decyl, undecyl, dodecyl, phenyl, C7 to C30 substituted phenyls, and all isomers thereof; more preferably $R^6$ is selected from hydrogen or from the group consisting of methyl, ethyl, n-propyl, iso-propyl, n-butyl, s-butyl, i-butyl, t-butyl, n-hexyl, cyclohexyl, phenyl, tolyl, mesityl, and naphthyl;

x is 0, 1, 2, 3, or 4 where x is typically the oxidation state of the metal minus 2;

each Z is, independently, a group 15 atom, preferably P or N, preferably N.

It is understood that the above formula encompass all possible stereoisomers, resonance structures and tautomers connoted by the structure of the formula.

In a particularly preferred embodiment, this invention relates to a transition metal compound represented by the formula (III):

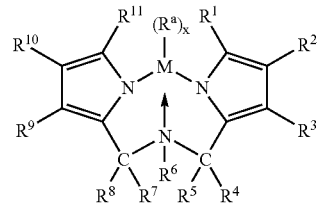

wherein
M is a Group 3 to 12 metal, preferably a Group 4, 5 or 6 metal, preferably Ti, Zr, Hf, V, or Cr, more preferably Ti, Zr, or Hf;
N is nitrogen;

each $R^a$ is, independently, a hydrogen, a hydrocarbyl group, a substituted hydrocarbyl group or halogen, preferably each $R^a$ is, independently, selected from the group consisting of chloride, bromide, fluoride, iodide, hydride, and C1 to C30 hydrocarbyls, preferably methyl, ethyl, propyl, butyl, pentyl, hexyl, phenyl, benzyl, and all isomers thereof;

each of $R^1$, $R^2$, $R^3$, $R^4$, $R^5$, $R^7$, $R^8$, $R^9$, $R^{10}$, and $R^{11}$ is, independently a hydrogen, a hydrocarbyl group, a substituted hydrocarbyl group or halogen, preferably each of $R^1$, $R^2$, $R^3$, $R^4$, $R^5$, $R^7$, $R^8$, $R^9$, $R^{10}$, and $R^{11}$ is, independently, selected from hydrogen or from the group consisting of C1 to C30 hydrocarbyls, preferably methyl, ethyl, propyl, butyl, pentyl, hexyl, heptyl, octyl, nonyl, decyl, undecyl, dodecyl, phenyl, C7 to C30 substituted phenyls, and all isomers thereof; more preferably each is, independently, selected from hydrogen or from the group consisting of methyl, ethyl, n-propyl, iso-propyl, n-butyl, s-butyl, i-butyl, t-butyl, n-hexyl, cyclohexyl, phenyl, tolyl, mesityl, and naphthyl;

$R^6$ is hydrogen, a hydrocarbyl group, a substituted hydrocarbyl group, preferably $R^6$ is selected from hydrogen or from the group consisting of C1 to C30 hydrocarbyls, preferably methyl, ethyl, propyl, butyl, pentyl, hexyl, heptyl, octyl, nonyl, decyl, undecyl, dodecyl, phenyl, C7 to C30 substituted phenyls, and all isomers thereof; more preferably $R^6$ is selected from hydrogen or from the group consisting of methyl, ethyl, n-propyl, isopropyl, n-butyl, s-butyl, i-butyl, t-butyl, n-hexyl, cyclohexyl, phenyl, tolyl, mesityl, and naphthyl; and x is 0, 1, 2, 3, or 4 where x is typically the oxidation state of the metal minus 2.

In a preferred embodiment, in Formula I, II or III, M is Ti, Zr or Hf. In another preferred embodiment, in Formula I, II or III, M is Ti, Zr, Hf, and each $R^a$ is selected from the group consisting of: hydrogen, methyl, ethyl, propyl, butyl, pentyl, hexyl, chlorine, iodine, and bromine.

In a preferred embodiment, the catalyst compound of this invention comprises one or more of [CH$_3$N(2-Et, 5-CH$_2$—C$_4$H$_3$N)$_2$]Ti(CH$_3$)$_2$; [CH$_3$N(2-Et, 5-CH$_2$—C$_4$H$_3$N)$_2$]Zr(CH$_3$)$_2$; or [CH$_3$N(2-Et, 5-CH$_2$—C$_4$H$_3$N)$_2$]Hf(CH$_3$)$_2$.

Activators and Activation Methods for Catalyst Compounds

The transition metal compounds, described above, are typically activated in various ways to yield compounds having a vacant coordination site that will coordinate, insert, and polymerize olefin(s). For the purposes of this patent specification and appended claims, the terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract one reactive, σ-bound, metal ligand making the metal complex cationic and providing a charge-balancing noncoordinating or weakly coordinating anion.

Aluminoxane and Aluminum Alkyl Activators

In one embodiment, alumoxane activators are utilized as an activator in the catalyst composition useful in the invention. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide, alkoxide or amide. Mixtures of different alumoxanes and modified alumoxanes may also be used.

Preferred activator compounds useful in this invention are represented by the following general formulae:

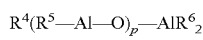

An alumoxane is generally a mixture of both the linear and cyclic compounds. In the general alumoxane formula, $R^3$, $R^4$, $R^5$ and $R^6$ are, independently a $C_1$-$C_{30}$ alkyl radical, for example, methyl, ethyl, propyl, butyl, pentyl, hexyl, heptyl, octyl, nonyl, decyl, and "p" is an integer from 1 to about 50. Most preferably, $R^3$, $R^4$, $R^5$ and $R^6$ are each methyl and "p" is a least 4. When an alkyl aluminum halide or alkoxide is employed in the preparation of the alumoxane, one or more $R^{3-6}$ groups may be halide or alkoxide.

It is recognized that alumoxane is not a discrete material. A typical alumoxane will contain free trisubstituted or trialkyl aluminum, bound trisubstituted or trialkyl aluminum, and alumoxane molecules of varying degree of oligomerization. Those methylalumoxanes most preferred contain lower levels of trimethylaluminum. Lower levels of trimethylaluminum can be achieved by reaction of the trimethylaluminum with a Lewis base or by vacuum distillation of the trimethylaluminum or by any other means known in the art. It is also recognized that after reaction with the transition metal compound, some alumoxane molecules are in the anionic form as represented by the anion in equations 4-6, thus for our purposes are considered "non-coordinating" anions.

For further descriptions, see U.S. Pat. Nos. 4,665,208, 4,952,540, 5,041;584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

When the activator is an alumoxane (modified or unmodified), some embodiments select the maximum amount of activator at a 10,000-fold molar excess Al/M over the catalyst precursor (per metal catalytic site). The minimum activator-to-catalyst-precursor is a 1:1 molar ratio.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another preferred alumoxane is a modified methyl alumoxane (MMAO) cocatalyst type 3A (commercially available from Akzo Chemicals, Inc. under the trade name Modified Methylalumoxane type 3A, described in U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared reacting a transition metal compound with some neutral Lewis acids, such as $B(C_6F_6)_3$, which upon reaction with the hydrolyzable ligand (X) of the transition metal compound forms an anion, such as $([B(C_6F_5)_3(X)]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

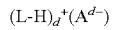
$(L-H)_d^+(A^{d-})$ wherein L is an neutral Lewis base;

H is hydrogen;
$(L-H)^+$ is a Bronsted acid
$A^{d-}$ is a non-coordinating anion having the charge d–
d is an integer from 1 to 3.

The cation component, $(L-H)_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene, and mixtures thereof. The activating cation $(L-H)_d^+$ may also be a moiety such as silver, tropylium, carbeniums, ferroceniums and mixtures, preferably carboniums and ferroceniums. Most preferably $(L-H)_d^+$ is triphenyl carbonium.

The anion component $A^{d-}$ include those having the formula $[M^{k+}Q_n]^{d-}$ wherein k is an integer from 1 to 3; n is an integer from 2-6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene (diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronapthyl)borate, triethylammonium tetrakis (perfluoronapthyl)borate, tripropylammonium tetrakis (perfluoronapthyl)borate, tri(n-butyl)ammonium tetrakis (perfluoronapthyl)borate, tri(t-butyl)ammonium tetrakis (perfluoronapthyl)borate, N,N-dimethylanilinium tetrakis (perfluoronapthyl)borate, N,N-diethylanilinium tetrakis (perfluoronapthyl)borate, N,N-dimethyl-(2,4,6-trimethylanilinium) tetrakis(perfluoronapthyl)borate, tropillium tetrakis(perfluoronapthyl)borate, triphenylcarbenium tetrakis(perfluoronapthyl)borate, triphenylphosphonium tetrakis(perfluoronapthyl)borate, triethylsilylium tetrakis(perfluoronapthyl)borate, benzene(diazonium) tetrakis (perfluoronapthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(t-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, benzene(diazonium) tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl) borate, and tri(2,6-dimethylphenyl)phosphonium tetrakis (pentafluorophenyl)borate.

Most preferably, the ionic stoichiometric activator $(L-H)_d^+$ $(A^{d-})$ is N,N-dimethylanilinium tetra(perfluorophenyl)borate, N,N-dimethylanilinium tetrakis(perfluoronapthyl)borate, N,N-dimethylanilinium tetrakis(perfluorobiphenyl)borate, N,N-dimethylanilinium tetrakis(3,5-bis (trifluoromethyl)phenyl)borate, triphenylcarbenium tetrakis (perfluoronapthyl)borate, triphenylcarbenium tetrakis (perfluorobiphenyl)borate, triphenylcarbenium tetrakis(3,5-bis(trifluoromethyl)phenyl)borate, or triphenylcarbenium tetra(perfluorophenyl)borate.

In one embodiment, an activation method using ionizing ionic compounds not containing an active proton but capable of producing a catalyst cation and their non-coordinating anion are also contemplated, and are described in EP-A-0 426 637, EP-A-0 573 403 and U.S. Pat. No. 5,387,568, which are all herein incorporated by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those that are compatible, stabilize the metallocene cation in the sense of balancing its ionic charge at +1, yet retain sufficient lability to permit displacement by an ethylenically or acetylenically unsaturated monomer during polymerization. These types of cocatalysts sometimes use tri-isobutyl aluminum or tri-octyl aluminum as a scavenger.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used with methylalumoxane.

Additional Activators

Other activators useful in this invention include those described in PCT publication WO 98/07515 such as tris (2,2', 2"-nonafluorobiphenyl) fluoroaluminate, which publication is fully incorporated herein by reference. Combinations of activators are also contemplated by the invention, for example, alumoxanes and ionizing activators in combinations, see for example, EP-B1 0 573 120, PCT publications WO 94/07928 and WO 95/14044 and U.S. Pat. Nos. 5,153, 157 and 5,453,410 all of which are herein fully incorporated by reference.

Other suitable activators are disclosed in WO 98/09996, incorporated herein by reference, which describes activating bulky ligand metallocene catalyst compounds with perchlorates, periodates and iodates including their hydrates. WO 98/30602 and WO 98/30603, incorporated by reference, describe the use of lithium (2,2'-bisphenyl-ditrimethylsilicate).4THF as an activator for a bulky ligand metallocene catalyst compound. WO 99/18135, incorporated herein by reference, describes the use of organo-boron-aluminum acitivators. EP-B1-0 781 299 describes using a silylium salt in combination with a non-coordinating compatible anion. Also, methods of activation such as using radiation (see EP-B1-0 615 981 herein incorporated by reference), electro-chemical oxidation, and the like are also contemplated as activating methods for the purposes of rendering the neutral bulky ligand metallocene catalyst compound or precursor to a bulky ligand metallocene cation capable of polymerizing olefins. Other activators or methods for activating a catalyst compound are described in for example, U.S. Pat. Nos. 5,849, 852, 5,859,653 and 5,869,723 and WO 98/32775, WO 99/42467 (dioctadecylmethylammonium-bis(tris(pentafluorophenyl)borane) benzimidazolide), which are herein incorporated by reference.

Another suitable ion forming, activating cocatalyst comprises a salt of a cationic oxidizing agent and a noncoordinating, compatible anion represented by the formula:

$$(OX^{e+})_d(A^{d-})_e \qquad (16)$$

wherein $OX^{e+}$ is a cationic oxidizing agent having a charge of e+; e is an integer from 1 to 3; and $A^-$, and d are as previously defined. Examples of cationic oxidizing agents include: ferrocenium, hydrocarbyl-substituted ferrocenium, $Ag^+$, or $Pb^{2+}$. Preferred embodiments of $A^{d-}$ are those anions previously defined with respect to the Bronsted acid containing activators, especially tetrakis(pentafluorophenyl)borate.

Activator Combinations

It within the scope of this invention that catalyst compounds can be combined with one or more activators or activation methods described above. For example, a combination of activators have been described in U.S. Pat. Nos. 5,153,157 and 5,453,410, European publication EP-B1 0 573 120, and PCT publications WO 94/07928 and WO 95/14044. These documents all discuss the use of an alumoxane in combination with an ionizing activator.

Supports, Carriers and General Supporting Techniques

The catalyst composition of the invention may, optionally, include a support material or carrier, and may also include a supported activator. For example, the catalyst composition component, the activator compound and/or the activated catalyst compound, may be deposited on, contacted with, vaporized with, bonded to, or incorporated within, adsorbed or absorbed in, or on, a support or carrier.

Support Material

The support material is any of the conventional support materials. Preferably, the supported material is a porous support material, for example, talc, inorganic oxides and inorganic chlorides. Other support materials include resinous support materials, such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those of Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference.

Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 µm. More preferably, the surface area of the support material is in the range of from about 50 to about 500 m$^2$/g, pore volume of from about 0.5 to about 3.5 cc/g and average particle size of from about 10 to about 200 µm. Most preferably, the surface area of the support material is in the range is from about 100 to about 400 m$^2$/g, pore volume from about 0.8 to about 3.0 cc/g and average particle size is from about 5 to about 100 µm. The average pore size of the carrier of the invention may be in the range of from 10 to 1000 Å, preferably 50 to about 500 Å, and most preferably 75 to about 350 Å.

The support materials may be treated chemically, for example with a fluoride compound as described in WO 00/12565, which is herein incorporated by reference. Other supported activators are described in for example WO 00/13792 that refers to supported boron containing solid acid complex.

In a particular embodiment, fumed silica available under the trade name Cabosil™ TS-610, available from Cabot Corporation is utilized as a nucleating agent or as a viscosity builder in the catalyst component slurry discussed below. Fumed silica is typically a silica with particles 7 to 30 nanometers in size that has been treated with dimethylsilyldichloride such that a majority of the surface hydroxyl groups are capped. In another embodiment, the fumed silica utilized has a particle size of less than 40 microns, preferably less than 20 microns or preferably less than 10 microns.

In a particular method of forming a supported catalyst composition component, the amount of liquid in which the activator is present is in an amount that is less than four times the pore volume of the support material, more preferably less than three times, even more preferably less than two times; preferred ranges being from 1.1 times to 3.5 times range and most preferably in the 1.2 to 3 times range. In an alternative embodiment, the amount of liquid in which the activator is present is from one to less than one times the pore volume of the support material utilized in forming the supported activator.

Procedures for measuring the total pore volume of a porous support are well known in the art. Details of one of these procedures is discussed in Volume 1, *Experimental Methods in Catalytic Research* (Academic Press, 1968) (specifically see pages 67-96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332-334 (March, 1956).

Supported Activators

In one embodiment, the catalyst composition includes a supported activator. Many supported activators are described in various patents and publications which include: U.S. Pat. No. 5,728,855 directed to the forming a supported oligomeric alkylaluminoxane formed by treating a trialkylaluminum with carbon dioxide prior to hydrolysis; U.S. Pat. Nos. 5,831, 109 and 5,777,143 discusses a supported methylalumoxane made using a non-hydrolytic process; U.S. Pat. No. 5,731,451 relates to a process for making a supported alumoxane by oxygenation with a trialkylsiloxy moiety; U.S. Pat. No. 5,856, 255 discusses forming a supported auxiliary catalyst (alumoxane or organoboron compound) at elevated temperatures and pressures; U.S. Pat. No. 5,739,368 discusses a process of heat treating alumoxane and placing it on a support; EP-A-0 545 152 relates to adding a metallocene to a supported alumoxane and adding more methylalumoxane; U.S. Pat. Nos. 5,756,416 and 6,028,151 discuss a catalyst composition of a alumoxane impregnated support and a metallocene and a bulky aluminum alkyl and methylalumoxane; EP-B1-0 662 979 discusses the use of a metallocene with a catalyst support of silica reacted with alumoxane; PCT WO 96/16092 relates to a heated support treated with alumoxane and washing to remove unfixed alumoxane; U.S. Pat. Nos. 4,912,075, 4,937, 301, 5,008,228, 5,086,025, 5,147,949, 4,871,705, 5,229,478, 4,935,397, 4,937,217 and 5,057,475, and PCT WO 94/26793 all directed to adding a metallocene to a supported activator; U.S. Pat. No. 5,902,766 relates to a supported activator having a specified distribution of alumoxane on the silica particles; U.S. Pat. No. 5,468,702 relates to aging a supported activator and adding a metallocene; U.S. Pat. No. 5,968,864 discusses treating a solid with alumoxane and introducing a metallocene; EP 0 747 430 A1 relates to a process using a metallocene on a supported methylalumoxane and trimethylaluminum; EP 0 969 019 A1 discusses the use of a metallocene and a supported activator; EP-B2-0 170 059 relates to a polymerization process using a metallocene and a organoaluminuim compound, which is formed by reacting aluminum trialkyl with a water containing support; U.S. Pat. No. 5,212,232 discusses the use of a supported alumoxane and a metallocene for producing styrene based polymers; U.S. Pat. No. 5,026,797 discusses a polymerization process using a solid component of a zirconium compound and a water-insoluble porous inorganic oxide preliminarily treated with alumoxane; U.S. Pat. No. 5,910,463 relates to a process for preparing a catalyst support by combining a dehydrated support material, an alumoxane and a polyfunctional organic crosslinker; U.S. Pat. Nos. 5,332,706, 5,473,028, 5,602,067 and 5,420,220 discuss a process for making a supported activator where the volume of alumoxane solution is less than the pore volume of the support material; WO 98/02246 discusses silica treated with a solution containing a source of aluminum and a metallocene; WO 99/03580 relates to the use of a supported alumoxane and a metallocene; EP-A1-0 953 581 discloses a heterogeneous catalytic system of a supported alumoxane and a metallocene; U.S. Pat. No. 5,015,749 discusses a process for preparing a polyhydrocarbyl-alumoxane using a porous organic or inorganic imbiber material; U.S. Pat. Nos. 5,446,001 and 5,534,474 relate to a process for preparing one or more alkylaluminoxanes immobilized on a solid, particulate inert support; and EP-A1-0 819 706 relates to a process for preparing a solid silica treated with alumoxane. Also, the following articles, also fully incorporated herein by reference for purposes of disclosing useful supported activators and methods for their preparation, include: W. Kaminsky, et al., "Polymerization of Styrene with Supported Half-Sandwich Complexes", Journal of Polymer Science Vol. 37, 2959-2968 (1999), describes a process of adsorbing a methylalumoxane to a support followed by the adsorption of a metallocene; Junting Xu, et al. "Characterization of isotactic polypropylene prepared with dimethylsilyl bis(1-indenyl)zirconium dichloride supported on methylaluminoxane pretreated silica", European Polymer Journal 35 (1999) 1289-1294, discusses the use of silica treated with methylalumoxane and a metallocene; Stephen O'Brien, et al., "EXAFS analysis of a chiral alkene polymerization catalyst incorporated in the mesoporous silicate MCM-41" Chem. Commun. 1905-1906 (1997), discloses an immobilized alumoxane on a modified mesoporous silica; and F. Bonini, et al., "Propylene Polymerization through Supported Metallocene/ MAO Catalysts: Kinetic Analysis and Modeling" Journal of Polymer Science, Vol. 33 2393-2402 (1995), discusses using a methylalumoxane supported silica with a metallocene. Any of the methods discussed in these references are useful for producing a supported activator component and all are incorporated herein by reference.

In another embodiment, the supported activator, such as supported alumoxane, is aged for a period of time prior to use herein. For reference please refer to U.S. Pat. Nos. 5,468,702 and 5,602,217, incorporated herein by reference.

In an embodiment, the supported activator is in a dried state or a solid. In another embodiment, the supported activator is in a substantially dry state or a slurry, preferably in a mineral oil slurry.

In another embodiment, two or more separately supported activators are used, or alternatively, two or more different activators on a single support are used.

In another embodiment, the support material, preferably partially or totally dehydrated support material, preferably 200° C. to 600° C. dehydrated silica, is then contacted with an organoaluminum or alumoxane compound. Preferably in an embodiment where an organoaluminum compound is used, the activator is formed in situ on and in the support material as a result of the reaction of, for example, trimethylaluminum and water.

In another embodiment, Lewis base-containing supports are reacted with a Lewis acidic activator to form a support bonded Lewis acid compound. The Lewis base hydroxyl groups of silica are exemplary of metal/metalloid oxides where this method of bonding to a support occurs. This embodiment is described in U.S. patent application Ser. No. 09/191,922, filed Nov. 13, 1998, which is herein incorporated by reference.

Other embodiments of supporting an activator are described in U.S. Pat. No. 5,427,991, where supported non-coordinating anions derived from trisperfluorophenyl boron are described; U.S. Pat. No. 5,643,847 discusses the reaction of Group 13 Lewis acid compounds with metal oxides such as silica and illustrates the reaction of trisperfluorophenyl boron with silanol groups (the hydroxyl groups of silicon) resulting in bound anions capable of protonating transition metal organometallic catalyst compounds to form catalytically active cations counter-balanced by the bound anions; immobilized Group IIIA Lewis acid catalysts suitable for carbocationic polymerizations are described in U.S. Pat. No. 5,288,677; and James C. W. Chien, Jour. Poly. Sci.: Pt A: Poly. Chem, Vol. 29, 1603-1607 (1991), describes the olefin polymerization utility of methylalumoxane (MAO) reacted with silica ($SiO_2$) and metallocenes and describes a covalent bonding of the aluminum atom to the silica through an oxygen atom in the surface hydroxyl groups of the silica.

In a particular embodiment, a supported activator is formed by preparing in an agitated, and temperature and pressure controlled vessel a solution of the activator and a suitable solvent, then adding the support material at temperatures from 0° C. to 100° C., contacting the support with the activator solution for up to 24 hours, then using a combination of heat and pressure to remove the solvent to produce a free flowing powder. Temperatures can range from 40 to 120° C. and pressures from 5 psia to 20 psia (34.5 to 138 kPa). An inert gas sweep can also be used in assist in removing solvent.

Alternate orders of addition, such as slurrying the support material in an appropriate solvent then adding the activator, can be used.

The catalyst compounds of this invention may be introduced into the reactor directly, in a solution, in a slurry, then may be combined with the activator before introduction into the reactor or after. In a preferred embodiment, the catalyst compound and optionally the activator are combined with mineral oil and then introduced into the rector. Likewise in another embodiment, the Catalyst compound, support and activator are combined with mineral oil and then introduced into the reactor. The catalyst and activator are preferably present at molar ratios of metal in the catalyst compound to metal in the activator of 1000:1 to 0.5 to 1, preferably 300:1 to 1:1, more preferably 150:1 to 1:1. In a preferred embodiment, the molar ratio of metal in the catalyst compound to metal in the activator, preferably alumoxanes, is 1:1 to 10:1

Monomers

The catalyst compounds described herein can be used to polymerize any monomer having two or more carbon atoms. Particularly preferred monomers include ethylene, propylene, butene, hexene, decene and octene. Useful monomers that can be polymerized by the catalyst compounds of this invention include $C_3$ to $C_{100}$ olefins, preferably $C_3$ to $C_{60}$ olefins, preferably $C_3$ to $C_{40}$ olefins preferably $C_3$ to $C_{20}$ olefins, preferably $C_3$ to $C_{12}$ olefins. In some embodiments preferred monomers include linear, branched or cyclic alpha-olefins, preferably $C_3$ to $C_{100}$ alpha-olefins, preferably $C_3$ to $C_{60}$ alpha-olefins, preferably $C_3$ to $C_{40}$ alpha-olefins preferably $C_3$ to $C_{20}$ alpha-olefins, preferably $C_3$ to $C_{12}$ alpha-olefins. Preferred olefin monomers may be one or more of propylene, butene, pentene, hexene, heptene, octene, nonene, decene, dodecene, 4-methyl-pentene-1,3-methyl pentene-1, 3,5,5-trimethyl hexene 1, and 5-ethyl-1-nonene.

Preferred monomers useful in this invention may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, paramethyl styrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane, norbornene, and the like.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In a preferred embodiment the catalyst compounds described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of propylene or a homopolymer of ethylene. In another preferred embodiment the polymer produced herein is a copolymer of propylene and one or more of ethylene, butene, pentene, hexene, heptene, octene, nonene, decene, dodecene, 4-methyl-pentene-1, 3-methyl pentene-1, and 3,5,5-trimethyl hexene 1. In another preferred embodiment the polymer produced herein is a copolymer of ethylene and one or more of propylene, butene, pentene, hexene, heptene, octene, nonene, decene, dodecene, 4-methyl-pentene-1, 3-methyl pentene-1, and 3,5,5-trimethyl hexene 1.

In a preferred embodiment the copolymers described herein comprise at least 50 mole % of a first monomer and up to 50 mole % of other monomers. In another embodiment, the copolymer comprises: 1) a first monomer present at from 40 to 95 mole %, preferably 50 to 90 mole %, preferably 60 to 80 mole %, and 2) a comonomer present at from 5 to 40 mole %, preferably 10 to 60 mole %, more preferably 20 to 40 mole %, and 3) a termonomer present at from 0 to 10 mole %, more preferably from 0.5 to 5 mole %, more preferably 1 to 3 mole %.

Polymerization Process

The catalyst systems described above are suitable for use in any prepolymerization and/or polymerization process over a wide range of temperatures and pressures. The temperatures may be in the range of from −60° C. to about 280° C., preferably from 50° C. to about 200° C., and the pressures employed may be in the range from 1 pa atmosphere to about 150 MPa or higher.

Polymerization processes include solution, gas phase, slurry phase, high pressure process, or supercritical phase or a combination thereof.

In one embodiment, the process of this invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1, 4-methyl-pentene-1, hexene-1, octene-1 and decene-1.

Gas Phase

The catalyst compounds of this invention can be used in a gas phase process to polymerize olefin monomers. In a gas phase polymerization process, a continuous cycle may be employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 600 psig (4138 kPa), preferably in the range of from about 200 psig (1379 kPa) to about 400 psig (2759 kPa), more preferably in the range of from about 250 psig (1724 kPa) to about 350 psig (2414 kPa). The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include series or multistage polymerization processes. Also gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421 all of which are herein fully incorporated by reference.

In a preferred embodiment, the reactor utilized in the present invention is capable of and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

Slurry Phase

A slurry polymerization process generally uses pressures in the range of from about 1 Pa to about 100 MPa atmospheres and even greater and temperatures in the range of 0° C. to about 120° C. In a slurry polymerization, a suspension of solid, particulate polymer is formed in a liquid polymerization diluent medium to which monomer (such as ethylene or propylene) and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A particularly useful polymerization technique in this invention is referred to as a particle form polymerization, or a slurry process where the temperature is kept below the temperature at which the polymer goes into solution. Such technique is well known in the art, and described in for instance U.S. Pat. No. 3,248,179, which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. Nos. 4,613,484 and 5,986,021, which are herein fully incorporated by reference.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Solution Phase

The catalysts described herein can be used advantageously in solution phase processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 30° C. and about 160° C., more preferably from about 90° C. to about 150° C., and most preferably from about 100° C. to about 140° C. Polymerization temperature may vary depending on catalyst choice. In series operation, the second reactor temperature may be higher or lower than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

In one embodiment 500 ppm or less of hydrogen is added to the polymerization, or 400 ppm or less or 300 ppm or less. In other embodiments at least 50 ppm of hydrogen is added to the polymerization, or 100 ppm or more, or 150 ppm or more.

Examples of solution processes are described in U.S. Pat. Nos. 4,271,060, 5,001,205, 5,236,998, 5,589,555 and 5,977, 251 and PCT WO 99/32525 and PCT WO 99/40130, which are fully incorporated herein by reference.

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor or plug flow reactor, or more than one reactor operated in series or parallel. These reactors may have or may not have internal cooling or heating and the monomer feed may or may not be refrigerated. See the general disclosure of U.S. Pat. No. 5,001,205 for general process conditions. See also, international application WO 96/33227 and WO 97/22639. All documents are incorporated by reference.

Polymer Products

The polymers produced by the process of the invention can be used in a wide variety of products and end-use applications. The polymers produced by the process of the invention include linear low density polyethylene, elastomers, plastomers, high density polyethylenes, medium density polyethylenes, low density polyethylenes, multimodal or bimodal high molecular weight polyethylenes, polypropylene and polypropylene copolymers.

The polymers, typically ethylene based polymers in one embodiment, have a density in the range of from 0.86 g/cc to 0.97 g/cc, depending on the desired use. For some applications, a density in the range of from 0.88 g/cc to 0.920 g/cc is preferred while in other applications, such as pipe, film and blow molding, a density in the range of from 0.930 g/cc to 0.965 g/cc is preferred. For low density polymers, such as for film applications, a density of 0.910 g/cc to 0.940 g/cc is preferred. Density is measured in accordance with standard ASTM methods.

The polymers produced herein may have a molecular weight distribution, a ratio of weight average molecular weight to number average molecular weight ($M_w/M_n$), of greater than 1.3 to about 70. In some embodiments the polymer produced has a narrow $M_w/M_n$ of about 1.3 to 15, preferably 1.5 to 4 while in other embodiments the polymer produced has an $M_w/M_n$ of about 30 to 50. Also, the polymers of the invention may have a narrow composition distribution as measured by Composition Distribution Breadth Index (CDBI as described in WO 93/03093, published Feb. 18, 1993, which is fully incorporated herein by reference, except that fractions having an Mw of 15,000 or less are ignored for our calculations). The polymers of the invention in one embodiment have CDBI's generally in the range of greater than 50% to 99%, preferably in the range of 55% to 85%, and more preferably 60% to 80%, even more preferably greater than 60%, still even more preferably greater than 65%.

The polymers of the present invention in one embodiment have a melt index (MI) or ($I_2$) as measured by ASTM-D-1238-E in the range from 0.01 dg/min to 1000 dg/min, more preferably from about 0.01 dg/min to about 100 dg/min, even more preferably from about 0.01 dg/min to about 50 dg/min, and most preferably from about 0.1 dg/min to about 10 dg/min.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

The polyolefins of the invention, particularly polypropylenes, can be made into films, molded articles (including pipes), sheets, wire and cable coating and the like. The films may be formed by any of the conventional techniques known in the art including extrusion, co-extrusion, lamination, blowing and casting. The film may be obtained by the flat film or tubular process which may be followed by orientation in a uniaxial direction or in two mutually perpendicular directions in the plane of the film to the same or different extents. Orientation may be to the same extent in both directions or may be to different extents. Particularly preferred methods to form the polymers into films include extrusion or coextrusion on a blown or cast film line.

EXAMPLES

Example 1

Preparation of [$CH_3N$(2-Et, 5-$CH_2$—$C_4H_3N$)$_2$]Ti($CH_3$)$_2$ ("Cat-A") Methyl lithium (15 ml of 1.4 M solution in ether) was added to a $-80°$ C. mixture of $TiCl_4$ (1.0 g in 60 mL of 1:5 pentane:ether) over the course of 10 minutes and the resulting mixture was stirred at $-80°$ C. for 3 hours. A solution of [$CH_3N$(2-Et, 5-$CH_2$—$C_4H_3NH$)$_2$] (1.29 g in 10 mL ether) was added and the solution was allowed to warm to room temperature slowly overnight. The mixture was filtered, the residue was extracted with ether (30 mL) and the combined ether filtrates were concentrated to give a red-brown solid. The solid was washed with pentane (2×50 mL) and dried under reduced pressure to give [$CH_3$ $N$(2-Et, 5-$CH_2$—$C_4H_3N$)$_2$ Ti($CH_3$)$_2$ as a brown solid (0.48 g, 30% yield).

Selected data is summarized below in Table 1.

Polymerization Reagents 1-hexene (97%) and 1-octene (98%) (Aldrich Chemical Company) were degassed by purging with nitrogen overnight and dried by stirring over NaK overnight followed by filtration through basic alumina (Aldrich Chemical Company, Brockman Basic 1) under nitrogen. Solvents, like toluene and hexanes, and ethylene (polymerization grade) were purified by passing through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves (Aldrich Chemical Company). TNOA (tri-n-octylaluminum, neat) from AKZO Nobel was used as received. Dimethylanilinium tetrakis(perfluorophenyl)borate ([DMAH][B(pfp)$_4$], [PhNMe$_2$H][B($C_6F_5$)$_4$]) was purchased from Albemarle Corporation and used without further purification.

Polymerizations

Ethylene-Octene co-polymerizations were performed in glass-lined 23.5 mL reactors equipped with disposable PEEK mechanical stirrers, an external heater for temperature control, septum inlet and regulated supply of nitrogen, ethylene, and propylene in an inert atmosphere of Nitrogen glove box. The reactor was dried and degassed at 115° C. for 5 hours and then purged with nitrogen at room temperature for another 5 hours. It was finally purged with ethylene.

For the polymerization examples the following reagent amounts and protocols were used: Hexane (2.55 mL), tri-n-octyl aluminum (1 micromol, 100 μL of 0.01M solution) and octene (200 μL) were added at room temperature. The reactor was heated to process temperature (105° C.) while stirring at 800 rpm. The activator (0.33 mL of a 0.6 mM toluene solution) and then the catalyst, (0.2 mL of a 1 mM toluene solution), were injected at process conditions.

Ethylene was fed to the reactor on demand to keep the pressure constant and the reaction was quenched with 5 mol % Oxygen in Argon after a predetermined amount of ethylene had been consumed. The reactor was then cooled, vented and the polymer recovered by vacuum centrifugation of the reaction mixture.

Characterization

For analytical testing, polymer sample solutions were prepared by dissolving the 2,6-di-tert-butyl-4-methylphenol (BHT, 99% purity was purchased from Aldrich) stabilized polymer in 1,2,4-trichlorobenzene (TCB 99+% purity from Aldrich; 5 gm of BHT in 4 L of TCB), at 160° C. in a shaker oven for approximately 3 hours. The typical concentration of polymer in solution was between 0.4 to 0.9 mg/mL. Samples were cooled to 135° C. for GPC testing.

Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). Samples were run in TCB at (135° C. sample temperatures, 160° C. oven/columns) using three Polymer Laboratories: PLgel 10 μm Mixed-B 300×7.5 mm columns in series. No column spreading corrections were employed. Numerical analyses were performed using Epoch® software available from Symyx Technologies.

Samples for infrared analysis were prepared by depositing the stabilized polymer solution onto a silanized wafer (Part number S10860, Symyx). By this method, approximately between 0.12 and 0.24 mg of polymer was deposited on the wafer cell. The samples were subsequently analyzed on a Brucker Equinox 55 FTIR spectrometer equipped with Pikes's MappIR specular reflectance sample accessory. Spectra, covering a spectral range of 5000 cm$^{-1}$ to 500 cm$^{-1}$, were collected at a 2 cm$^{-1}$ resolution with 32 scans.

For ethylene-octene copolymers, the wt. % copmonomer is determined via measurement of the methyl deformation band at ~1375 cm$^{-1}$. The peak height of this band is normalized by the combination and overtone band at ~4321 cm$^{-1}$, which corrects for path length differences. The normalized peak height is correlated to individual calibration curves from H-NMR data to predict the wt. % comonomer content within a concentration range of ~2 to 25 wt. % for butene and hexene and ~2 to 35 wt. % for octene. Typically, R$^2$ correlations of 0.98 or greater are achieved.

TABLE 1

| Catalyst | Activator | Mw | Mw/Mn | Wt % octene | Activity (g polymer/mmol catalyst · hour) |
|---|---|---|---|---|---|
| Cat-A | A | 352,000 | 1.6 | 2 | 5077 |
| Cat-A | A | 361,000 | 1.6 | 3 | 4724 |
| Cat-A | A | 381,000 | 1.6 | 2 | 3457 |
| Cat-A | B | 412,000 | 1.6 | 3 | 3332 |
| Cat-A | B | 457,000 | 1.6 | 3 | 2377 |
| Cat-A | B | 421,000 | 1.6 | 3 | 1806 |

Activator A is N,N-dimethylanilinium perfluorotetraphenyl borate ([PhN(H)Me$_2$][(C$_6$F$_5$)$_4$B]) and Activator B is triphenylcarbenium perfluorotetraphenyl borate ([Ph$_3$C][(C$_6$F$_5$)$_4$B]).

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby.

The invention claimed is:

1. A compound represented by the formula:

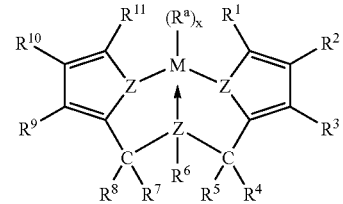

wherein:
M is a Group 3 to 12 transition metal;
each R$^a$ is, independently, selected from the group consisting of chloride, bromide, fluoride, iodide, and C1 to C30 hydrocarbyls;
each of R$^1$, R$^2$, R$^3$, R$^4$, R$^5$, R$^7$, R$^8$, R$^9$, R$^{10}$, and R$^{11}$ is, independently a hydrogen, a hydrocarbyl group, a substituted hydrocarbyl group or halogen;
R$^6$ is hydrogen, a hydrocarbyl group, or a substituted hydrocarbyl group;
x is 1, 2, 3 or 4; and
each Z is, independently, a group 15 atom.

2. The compound of claim 1 wherein each Z is nitrogen.

3. The compound of claim 1 wherein M is a Group 4 to 11 metal.

4. The compound of claim 1 wherein M is a Group 4 to 9 metal.

5. The compound of claim 1 wherein M is a Group 4 to 6 metal.

6. The compound of claim 1 wherein M is Ti, Zr, Hf, V, Cr, Fe, Co or Ni.

7. The compound of claim 1 wherein M is Ti, Zr, or Hf.

8. The compound of claim 1 wherein each R$^a$ is, independently, selected from the group consisting of methyl, ethyl, propyl, butyl, pentyl, hexyl, phenyl, benzyl, and all isomers thereof.

9. The compound of claim 1 wherein each of $R^1$, $R^2$, $R^3$, $R^4$, $R^5$, $R^7$, $R^8$, $R^9$, $R^{10}$, and $R^{11}$ is, independently, selected from hydrogen or from the group consisting of C1 to C30 hydrocarbyls.

10. The compound of claim 1 wherein each of $R^1$, $R^2$, $R^3$, $R^4$, $R^5$, $R^7$, $R^8$, $R^9$, $R^{10}$, and $R^{11}$ is, independently, selected from hydrogen or from the group consisting of methyl, ethyl, propyl, butyl, pentyl, hexyl, heptyl, octyl, nonyl, decyl, undecyl, dodecyl, phenyl, C7 to C30 substituted phenyls, and all isomers thereof.

11. The compound of claim 1 wherein each of $R^1$, $R^2$, $R^3$, $R^4$, $R^5$, $R^7$, $R^8$, $R^9$, $R^{10}$, and $R^{11}$ is, independently, selected from hydrogen or from the group consisting of methyl, ethyl, n-propyl, iso-propyl, n-butyl, s-butyl, i-butyl, t-butyl, n-hexyl, cyclohexyl, phenyl, tolyl, mesityl, and naphthyl.

12. The compound of claim 1 wherein $R^6$ is selected from hydrogen or from the group consisting of C1 to C30 hydrocarbyls.

13. The compound of claim 1 wherein $R^6$ is selected from methyl, ethyl, propyl, butyl, pentyl, hexyl, heptyl, octyl, nonyl, decyl, undecyl, dodecyl, phenyl, C7 to C30 substituted phenyls, and all isomers thereof.

14. The compound of claim 1 wherein $R^6$ is selected from hydrogen or from the group consisting of methyl, ethyl, n-propyl, iso-propyl, n-butyl, s-butyl, i-butyl, t-butyl, n-hexyl, cyclohexyl, phenyl, tolyl, mesityl, and naphthyl.

15. The compound of claim 1 wherein M is Ti, Zr, Hf, and each $R^a$ is selected from the group consisting of: methyl, ethyl, propyl, butyl, pentyl, hexyl, fluorine, chlorine, iodine, and bromine.

16. The compound of claim 1 wherein the compound comprises one or more of $[CH_3N(2-Et, 5-CH_2—C_4H_3N)_2]Ti(CH_3)_2$; $[CH_3N(2-Et, 5-CH_2—C_4H_3N)_2]Zr(CH_3)_2$; or $[CH_3N(2-Et, 5-CH_2—C_4H_3N)_2]Hf(CH_3)_2$.

17. A supported catalyst compound comprising a support and the compound of claim 1.

18. The supported catalyst compound of claim 17, where the support comprises silica.

19. A catalyst system comprising the compound of claim 1 and an activator.

20. The catalyst system of claim 19 wherein the activator comprises an alumoxane.

21. The catalyst system of claim 19 wherein the activator comprises methylalumoxane.

22. The catalyst system of claim 19 wherein the activator comprises modified methylalumoxane.

23. The catalyst system of claim 19 wherein the activator comprises an ionizing activator.

24. The catalyst system of claim 19 wherein the activator comprises a non-coordinating anion.

25. The catalyst system of claim 19 wherein the activator comprises one or more of: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis (pentafluorophenyl)borate, tri(n-butyl)ammonium tetrakis (pentafluorophenyl)borate, tri(sec-butyl)ammonium tetrakis (pentafluorophenyl)borate, N,N-dimethylanilinium tetrakis (pentafluorophenyl)borate, N,N-diethylanilinium tetrakis (pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl) ammonium tetrakis-(2,3,4,6-tetrafluoro-phenyl)borate, dimethyl(t-butyl)ammonium tetrakis-(2,3,4,6tetrafluorophenyl) borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronapthyl)borate, triethylammonium tetrakis (perfluoronapthyl)borate, tripropylammonium tetrakis (perfluoronapthyl)borate, tri(n-butyl)ammonium tetrakis (perfluoronapthyl)borate, tri(t-butyl)ammonium tetrakis (perfluoronapthyl)borate, N,N-dimethylanilinium tetrakis (perfluoronapthyl)borate, N,N-diethylanilinium tetrakis (perfluoronapthyl)borate, N,N-dimethyl-(2,4,6-trimethylanilinium) tetrakis(perfluoronapthyl)borate, tropillium tetrakis(perfluoronapthyl)borate, triphenylcarbenium tetrakis(perfluoronapthyl)borate, triphenylphosphonium tetrakis(perfluoronapthyl)borate, triethylsilylium tetrakis(perfluoronapthyl)borate, benzene(diazonium) tetrakis (perfluoronapthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium) tetrakis(3,5-bis(trifluoromethyl)phenyl)borate, di-(i-propyl)ammonium tetrakis (pentafluorophenyl)borate, and dicyclohexylammonium tetrakis(pentafluorophenyl)borate, as tri(o-tolyl)phosphonium tetrakis(pentafluorophenyl)borate, tri(2,6-dimethylphenyl)phosphonium tetrakis(pentafluorophenyl)borate, tris (2,2', 2"-nonafluorobiphenyl) fluoroaluminate, or dioctadecylmethylammonium-bis(tris(pentafluorophenyl)borane) benzimidazolide.

26. The catalyst system of claim 19 wherein the activator comprises one or more of: N,N-dimethylanilinium tetra(perfluorophenyl)borate, N,N-dimethylanilinium tetrakis(perfluoronapthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronapthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

27. A process to polymerize monomers comprising contacting the compound of claim 1 with an activator and monomers.

28. A process to polymerize monomers comprising contacting the catalyst system of claim 19 with monomers.

29. The process of claim 27 wherein the monomers comprise olefins.

30. The process of claim 28 wherein the olefins comprise ethylene.

31. The process of claim 27 wherein the olefins comprise propylene.

32. The process of claim 28 wherein the olefins comprise ethylene and propylene.

33. The process of claim 29 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

34. The process of claim 27 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

35. The process of claim 27 wherein the polymerization occurs in the gas phase.

36. The process of claim 27 wherein the polymerization occurs in the slurry phase.

37. The process of claim 27 wherein the polymerization occurs in the solution phase.

* * * * *